United States Patent [19]

Schwender et al.

[11] 4,066,767
[45] Jan. 3, 1978

[54] 8-(1H-TETRAZOL-5-YL)-11H-PYRIDO[2,1-B]QUINAZOLIN-11-ONES AND METHOD OF TREATING BRONCHIAL ASTHMA USING THEM

[75] Inventors: Charles F. Schwender, Lebanon; Brooks R. Sunday, Hackettstown, both of N.J.

[73] Assignee: Warner-Lambert Company, Morris Plains, N.J.

[21] Appl. No.: 737,878

[22] Filed: Nov. 1, 1976

[51] Int. Cl.$^2$ .................. A61K 31/505; C07D 471/04
[52] U.S. Cl. .............................. 424/251; 260/251 A; 260/256.4 F
[58] Field of Search ................. 260/251 A, 256.4 F; 424/251

[56] References Cited

U.S. PATENT DOCUMENTS

| | | | |
|---|---|---|---|
| 3,966,965 | 6/1976 | Sellstedt et al. | 424/309 |
| 3,982,000 | 9/1976 | Hardtmann | 424/251 |
| 4,012,387 | 3/1977 | Schwender et al. | 260/251 A |
| 4,033,961 | 7/1977 | Schwender et al. | 260/251 A |

OTHER PUBLICATIONS

Laboratories U.P.S.A., Chemical Abstracts, 64, 712h–713d (1966).

Primary Examiner—R. J. Gallagher
Assistant Examiner—Diana G. Rivers
Attorney, Agent, or Firm—Albert H. Graddis; Frank S. Chow; George M. Yahwak

[57] ABSTRACT

The present invention relates to 8-(1H-tetrazol-5-yl)-11H-pyrido[2,1-b]quinazolin-11-ones having the following structure:

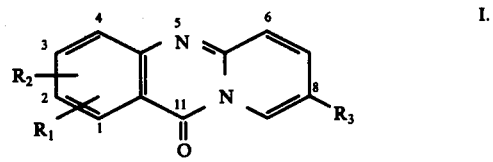

wherein $R_1$ and $R_2$ are hydrogen, alkyl, alkyloxy, halogen, hydroxy and methylenedioxy; $R_3$ is carboxamido, cyano or 5-tetrazolyl groupings and the pharmaceutically acceptable salts of acids and bases thereof.

These compounds exhibit anti-allergic properties and are useful as anti-asthmatic agents.

7 Claims, No Drawings

8-(1H-TETRAZOL-5-YL)-11H-PYRIDO[2,1-B]QUINAZOLIN-11-ONES AND METHOD OF TREATING BRONCHIAL ASTHMA USING THEM

The present invention relates to 8-(1H-tetrazol-5-yl)-11H-pyrido[2,1-b]quinazolin-11-ones having the following structural formula:

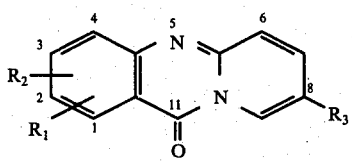

wherein $R_1$ and $R_2$ are hydrogen, alkyl, alkyloxy, halogen, hydroxy and methylenedioxy; $R_3$ is carboxamido, cyano or 5-tetrazolyl groupings and the pharmaceutically acceptable salts of acids and bases thereof.

In the above definitions for $R_1 - R_3$, alkyl and the alkyl portion in alkyloxy are meant to have 1 – 4 carbon atoms, e.g., methyl, ethyl, propyl, isopropyl, butyl and isobutyl. The term "halogen" includes all the four members, i.e., fluorine, chlorine, bromine, and iodine.

The preferred compounds of the present invention falling within the above generic description are:

$R_1R_2$=H and $R_3$ = 5-tetrazolyl
$R_1$ = 2—OCH$_3$, $R_2$= H, $R_3$= 5-tetrazolyl
$R_1$ = 2—CH$_3$, $R_2$ = H, $R_3$ = 5-tetrazolyl
$R_1$, $R_2$ =2,3-di-OCH$_3$, $R_3$= 5-tetrazolyl
$R_1$ = 2—OH, $R_2$= H, $R_3$ = 5-tetrazolyl The compounds of this invention having the generic formula I above, have been found to reduce allergic responses to antigen challenge by inhibiting antibody-antigen reactions in mammals such as rats. When tested in accordance with the procedure of Herzig [*Immunopharmacology*, M. E. Rosenthale and H. C. Mansmann, Eds., John Wiley and Son, N.Y., 1975], these compounds inhibit allergic responses or passive cutaneous anaphylaxis (PCA) in the rat when administered orally, parenterally or by aerosol at a dose of 0.001–20 mg/kg. Accordingly, these compounds are indicated in the management of allergic conditions such as bronchial asthma. Generally speaking, in an adult human, a dose of 0.001–20 mg/kg orally, parenterally or by aerosol administration 1 to 3 times daily is suggested for the relief of bronchial asthma. As with anti-allergy treatment, the dose is to be adjusted for individual needs but is within the above range.

The compounds of this invention are more potent and orally effective over previously known compounds such as cromolyn sodium.

Thus, for example, cromolyn sodium in the aforesaid PCA test was found to be orally inactive whereas the instant compounds were found to be orally active. Parenterally, the instant compounds were also found to be more potent than cromolyn sodium.

According to the present invention, the aforesaid Compound I is prepared in three steps:

An approximately substituted anthranilic acid is condensed with one equivalent of 6-chloronicotinamide in acetic acid to give the corresponding substituted pyrido[2,1-b]quinazolinone-8-carboxamide intermediate. The carboxamide is dehydrated to the nitrile derivative using p-toluenesulfonyl chloride in pyridine and DMF. The tetrazolyl product is obtained from the nitrile using NaN$_3$, NH$_4$Cl and DMF.

The corresponding salts are prepared by reacting the parent compound with an appropriate base, e.g., sodium bicarbonate, potassium bicarbonate or an acid, e.g., hydrochloric, hydrobromic, hydrosulfuric, by methods well-known in the art.

To further illustrate the practice of this invention, the following examples are included:

EXAMPLE 1

8-Carboxamido-2-methoxy-11-oxo-11(1H)-pyrido[2,1-b] quinazoline.

A mixture of 5-methoxy-anthranilic acid (27.0 g, 161 mmol), 6-chloro-nicotinamide (25.0 g, 160 mmol) and ethanol (500 ml) containing 15 ml of concentrated HCl was heated at reflux for 24 hours. The mixture was cooled to 0° and the resultant solid precipitate was collected by filtration to give 34.0 g (69.5%) of crude hydrochloride salt. This material was recrystallized twice from pyridine to give the analytical sample, m.p. 329°–32° dec.

EXAMPLE 2

8-Cyano-2-methoxy-11-oxo-11(H)-pyrido[2,1-b]quinazoline

A solution of 1.2 l. pyridine, 300 ml of DMF, 7.46 g (39.4 mmol) of p-toluenesulfonyl chloride and 7.45 g (27.6 mmol) of 8-carboxamido-2-methoxy-11-oxo-11(H)-pyrido[2,1-b]quinazoline was heated at 100° for 42 hours. The mixture was cooled and poured into 4 l. ice/H$_2$O and acidified to pH 1 with concentrated HCl. The solid which formed was collected; yield, 5.0 g (72.2%), m.p. 273°–280° dec. The analytically pure nitrile was obtained after one recrystallization from pyridine, m.p. 281°–285° dec.

EXAMPLE 3

2-Methoxy-8-(1H-tetrazol-5-yl)-11-oxo-11(H)pyrido[2,1-b]-quinazoline.

A mixture of 3.00 g (12 mmol) of 8-cyano-2-methoxy-11-oxo-11(H)-pyrido[2,1-b]quinazoline, NaN$_3$ (2.22 g, 34.2 mmol), NH$_4$Cl (1.83 g, 34.2 mmol) and 250 ml of DMF was heated at 115° for 20 hours. The mixture was cooled, poured onto 1.5 l. of ice/H$_2$O and acidified with concentrated HCl. The solid which formed was collected; yield, 2.93 g (83%), m.p. 279°–299° dec. The sample of analytical purity was obtained by recrystallization from pyridine; yield, 2.25 g (64%), m.p. 302°–304° dec.

Other compounds of the present invention are prepared in an analogous manner.

The physical characteristics of the compounds of the present invention are set out in the following Table:

TABLE

| $R_4$ | $R_5$ | m.p. ° dec. | Formula | Elemental Analysis | Solvent of Recryst. |
|---|---|---|---|---|---|
| H | 8-$CONH_2$ | 338–44 | $C_{13}H_9N_3O_2$ | CHN | pyridine |
| H | 8-CN | 249–51 | $C_{13}H_7N_3O \cdot \frac{1}{2}H_2O$ | CHN | pyridine |
| H | 8-(5-tetrazolyl) | 293–96 | $C_{13}H_8N_6O \cdot \frac{1}{4}C_2H_6O$ | CHN | EtOH |
| 2-$CH_3$ | 8-$CONH_2$ | 332–36 | $C_{14}H_{11}N_3O_2$ | CHN | pyridine |
| 2-$CH_3$ | 8-CN | 307–09 | $C_{14}H_9N_3O$ | CHN | pyridine |
| 2-$CH_3$ | 8-(5-tetrazolyl) | 284–86 | $C_{14}H_{10}N_6O_2$ | CHN | pyridine |
| 2-$OCH_3$ | 8-$CONH_2$ | 329–32 | $C_{14}H_{11}N_3O_2$ | CHN | pyridine |
| 2-$OCH_3$ | 8-CN | 281–85 | $C_{14}H_9N_3O_2$ | CHN | pyridine |
| 2-$OCH_3$ | 8-(5-tetrazolyl) | 302–04 | $C_{14}H_{10}N_6O_2$ | CHN | pyridine |
| 3-$OCH_3$ | CN | 273–75 | $C_{14}H_9N_3O_2$ | CHN | pyridine |
| 3-$OCH_3$ | 8-(5-tetrazolyl) | 284–87 | $C_{14}H_{10}N_6O_2$ | CHN | pyridine |
| 2,3-di $OCH_3$ | $CONH_2$ | 313–18 | $C_{15}H_{13}N_3O_4 \cdot \frac{1}{2}H_2O$ | CHN | pyridine |
| 2,3-di $OCH_3$ | CN | 309–12 | $C_{15}H_{11}N_3O_3 \cdot \frac{1}{2}H_2O$ | CHN | pyridine |
| 2,3-di $OCH_3$ | 8-(5-tetrazolyl) | 300–303 | $C_{15}H_{12}N_6O_3$ | CHN | pyridine |
| 2,3-methylenedioxy | $CONH_2$ | 368–73 | $C_{14}H_9N_3O_4$ | CHN | pyridine |
| 2,3-methylenedioxy | CN | 319–23 | $C_{14}H_7N_3O_3$ | CHN | pyridine |
| 2,3-methylenedioxy | 8-(5-tetrazolyl) | 310–13 | $C_{14}H_8N_6O_3$ | CHN | pyridine |
| 2-Cl | $CONH_2$ | 326–30 | $C_{13}H_8ClN_3O_2$ | CHNCl | pyridine |
| 2-OH | $CONH_2$ | 346–52 | $C_{13}H_9N_3O_3$ | CHN | pyridine |

What we claim is:
1. A compound of the formula:

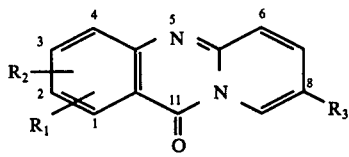

I.

wherein $R_1$ and $R_2$ are hydrogen, halogen, hydroxy, methylenedioxy or lower alkyl or alkoxy of 1 to 4 carbons; $R_3$ is 5-tetrazolyl and the pharmaceutically acceptable salts thereof.

2. A compound according to claim 1 in which $R_1$ and $R_2$ are hydrogen and $R_3$ is 8-(5-tetrazolyl).

3. A compound according to claim 1 in which $R_1$ is 2—$CH_3$, $R_2$ is hydrogen and $R_3$ is 8-(5-tetrazolyl).

4. A compound according to claim 1 in which $R_1$ is 2—$OCH_3$, $R_2$ is hydrogen and $R_3$ is 8-(5-tetrazolyl).

5. A compound according to claim 1 in which $R_1$ is 2—$OCH_3$, $R_2$ is 3-$OCH_3$ and $R_3$ is 8-(5-tetrazolyl).

6. A compound according to claim 1 in which $R_1$ and $R_2$ together is 2,3-methylenedioxy and $R_3$ is 8-(5-tetrazolyl).

7. A method for the treatment of bronchial asthma in a mammal suffering from asthma which comprises the administration of an anti-asthmatically effective amount of a compound according to claim 1 at an adult human dose of 0.001–20 mg/kg orally, parenterally, or by aerosol.

* * * * *

Notice of Adverse Decision in Interference

In Interference No. 100,005, involving Patent No. 4,066,767, C. F. Schwender and B. R. Sunday, 8-(1H-TETRAZOL-5-YL)-11H-PYRIDO[2,1-B]QUINAZOLIN-11-ONES AND METHOD OF TREATING BRONCHIAL ASTHMA USING THEM, final judgment adverse to the patentees was rendered Dec. 18, 1979, as to Claim 4.

[*Official Gazette, April 29, 1980.*]

UNITED STATES PATENT OFFICE
CERTIFICATE OF CORRECTION

Patent No. 4,066,767                Dated January 3, 1978

Inventor(s) Charles F. Schwender et al.

It is certified that error appears in the above-identified patent and that said Letters Patent are hereby corrected as shown below:

IN THE SPECIFICATION:

Column 1, line 67 delete "approximately" and insert --- appropriately ---.

IN THE CLAIMS:

Claims 2,3,4,5, and 6, second line, "8-(5-tetrazolyl)", each occurrence, should read --- 5-tetrazolyl ---

Signed and Sealed this

Nineteenth Day of August 1980

[SEAL]

Attest:

SIDNEY A. DIAMOND

Attesting Officer      Commissioner of Patents and Trademarks